United States Patent [19]

Krishtal

[11] Patent Number: 5,449,492
[45] Date of Patent: Sep. 12, 1995

[54] DEVICE FOR DETERMINING CONCENTRATION-DEPENDENT ELECTROPHYSIOLOGICAL PARAMETERS IN A SERIES OF MEASUREMENTS

[75] Inventor: Oleg A. Krishtal, Kiev, Ukraine

[73] Assignee: List Electronics, Darmstadt, Germany

[21] Appl. No.: 143,394

[22] Filed: Oct. 25, 1993

Related U.S. Application Data

[63] Continuation of Ser. No. 820,839, Jan. 15, 1992, abandoned.

[51] Int. Cl.$^6$ .................... G01N 35/02; G01N 27/31
[52] U.S. Cl. ........................... 422/64; 422/63; 422/67; 422/68.1; 422/82.02; 435/291
[58] Field of Search ............. 422/63, 64, 65, 66, 422/67, 68.1, 75, 82.02; 436/45, 47, 48, 49, 51; 435/29, 30, 291

[56] References Cited

U.S. PATENT DOCUMENTS

| | | | |
|---|---|---|---|
| 4,101,383 | 7/1978 | Wyatt et al. | 195/103.5 |
| 4,595,562 | 6/1986 | Liston et al. | 422/65 |
| 4,629,703 | 12/1986 | Uffenheimer | 422/63 X |
| 4,711,851 | 12/1987 | McNamara et al. | 435/287 |
| 4,951,512 | 8/1990 | Mazza et al. | 73/861.23 |

FOREIGN PATENT DOCUMENTS 0128527 12/1984 European Pat. Off. .
WO89/10556 11/1989 WIPO .

OTHER PUBLICATIONS

Criado et al., "A membrane Fusion Strategy for Single-Channel Recordings of Membranes Usually No-n-Accessible to Patch-Clamp Pipette," FEBS Letters 05296, vol. 224 (1), Nov. 1987, 172–76.

Hamill et al., "Improved Patch-Clamp Techniques for High-Resolution Current Recording from Cells and Cell-Free Membrane Patches", *Pflugers Archiv.*, (1981) 391 85–100.

*Primary Examiner*—Donald E. Czaja
*Assistant Examiner*—Milton I. Cano
*Attorney, Agent, or Firm*—Robbins, Berliner & Carson

[57] ABSTRACT

The determination of concentration-dependent parameters in a series of measurements, in particular for the determination of dose-effect correlations, the solutions to be developed are each contained in chambers positioned on a round tray in radial symmetrically arrangement. The respective chamber just to be determined is moved underneath the measuring device via a gyratory movement of a round tray controlled by a computer and the vertical disk between the measuring device at the chamber to be measured is also lowered by computerized control so far until the measuring device dives into the solution in the chamber. The device to realize the process comprises a horizontally rotatable round tray as well as a lifting device wherewith either the total round tray including all chambers positioned thereupon can be vertically moved or only that chamber being immediately positioned underneath the measuring device. The measuring device is composed of a measuring cell comprising a suction tube in which the solution to be measured is sucked and a measuring system projecting into said tube. In particular, the process and the device are suited to measure series of concentrations where a reactant, in particular a bioindicator, constantly loses activity in a run of a series of measurements.

2 Claims, 1 Drawing Sheet

DEVICE FOR DETERMINING CONCENTRATION-DEPENDENT ELECTROPHYSIOLOGICAL PARAMETERS IN A SERIES OF MEASUREMENTS

This is a continuation of Ser. No. 07/820,839 filed Jan. 15, 1992, now abandoned.

The present invention deals with a process and a device for the quick determination of concentration-dependent parameters in a series of measurements containing solutions of chemical substances correlated to said parameters, the measuring device being immersed into the solutions located in chambers (dishes), each having a different concentration of a chemical substance and the subsequent determination of the parameters being dependent from each concentration of the chemical substance.

In determining measured values wherewith concentration-dependent effects of interacting chemical compounds or of chemical compounds affecting living systems shall be examined, a person skilled in the art is often confronted with the problem that a reactant or indicator constantly loses activity during the run of the series of measurements.

If there are only determined concentration dependencies of chemicals compounds, the problem can be circumvented under considerable loss of time by freshly formulating each single charge to be measured shortly before measuring or, if in each case the damping behavior of one or other reactant or indicator allows, by preparing a new formulation of only a part of the series of measurements; in keeping the external conditions constant, chemical compounds will react reproducibly equally.

There is a different way in using bioindicators, e.g. in the form of cell suspensions, of single isolated cells or even of cell particles. Here, it must be assumed that the single bioindicators, having defined outer conditions, will react in each case with a different sensitivity upon the concentration-dependent chemical stimulations to be determined, that means, the bioindicator for the measuring of a run of a series of measurements should not be exchanged.

A newly developed method for the determination of dose-effect-relations of biologically active substances is representative thereof: "concentration-clamp method". Therein, electro-physiological parameters, especially ionic currents or ionic conductivities of membranes of isolated single cells or membrane patches respectively are determined as a function of the concentration of biologically active substances affecting the cell or the patch.

The method takes advantage from the fact that cell membranes are principally constituting electric capacitors in which an inequality of the ion distribution is maintained by means of ATP-energy. The ions are transported through ion channels (pores) by means of carriers (ionophores) being specific for each type of ions (biological ionophoresis). In case of stimulation by chemical substances, activators or ions are recognized by macromolecular receptors on the surface of the membranes and an activator-receptor complex is first built up. Thereby, an activating mechanism is triggered where the ions, following the gradient of concentration and load, flow into the cell ($Na^+$, $Ca^{2+}$) or out of it ($K^+$) through ion channels being assigned thereto. As a consequence, the membrane is depolarized.

Such electrophysiological effects of the membrane as a reaction to electrical or chemical stimulations can be evaluated quantitatively, with isolated single cells as well as with membrane patches. In using the latter method, on the tip of a pipette (having an opening of normally $<=1$ um) a membrane patch is positioned ($<=1$ $um^2$), at which the potential and time-dependent ionic currents are determined (patch-clamp method). In case that the membrane patch is mounted thus that the initial outer surface of the membrane points outwardly away from the tip of pipette, the inner surface of the membrane patch then being surrounded by a solution inside the pipette and corresponding to the intracellular environment, the reaction of the membrane channels responding to charges in the extracellular envornment can be persued by determination of the electrophysiological parameters (voltage-clamp method).

Since the biologically active substances are directly interacting with the receptors, by determination of membrane currents, predicates can be obtained referring to dissociation and association constants of chemical substances and receptors which suggest an activating or inactivating effect. On the other hand, chemical substances can directly react with ionophores (ion-transmitter substances) thereby interfering with the ion transport, which fact leads to a desensibilization or an inhibition. Moreover, by determination of different concentrations of substances, predicates can be obtained referring to kinetics of activation or desensibilization of these membranes.

In correlating the thereby determined electrophysiological parameters as a function of the concentration of the substances affecting the cell or membrane patch with known phenotypical effects of said substances, there can be made prognostications as regards the biological activity of substances of which the effect on cells was so far unknown, or there can be obtained criteria for defining borderline concentrations of chemical compounds the toxicity of which has not yet been appraisable.

However, in determining such series of concentrations of chemical substances by use of bioindicators, in order to obtain dose-effect-relations, there are required preconditions which could not be kept in accordance with the previous state of the art:

a) since the actual vitality of the bioindicators in the form of a cell or a membrane patch highly depends from the respective dissecting method, from the dexterity of the experimentalist, from the quality and maturity of each cell suspension out of which the cell or membrane patch has been acquired, for reasons of reproducibility, an appropriate interpretation and comparison of the measured values is only practicable in case that the total series of concentrations is determined in using one and the same cell or membrane patch respectively;

b) since the bioindicator has only a limited service life to obtain significant measure values, that means that its vitality is constantly decreasing, the total series of concentrations must be determined within said stretch of time;

c) since the optimal ascension of the single concentrations within a series of concentrations, i.e. the concentration gradient, can only be developed during a run of a series of measurements that already takes place, diverse charges of concentration should be exchangeable in the course of a run of a series of measurements that already takes place;

d) since the decrease of the vitality of a bioindicator depends from each bioindicator used and from each preparation, the actual degree of the decrease of the vitality of the bioindicator used should be determined in the course of the series of concentrations;

e) since interpretations of dose-effect-relations are becoming all the detailed the more concentrations and the more frequently the single charges of each run of a series of concentrations can be determined within the stretch of time being available, there should be the feasibility of a throughput rate per time unit as great as possible.

In order to perform such screening tests according to the technique of prior art, the concentration charges being contained in dishes or test tubes have been moved beneath the device by hand or there have been utilized standardized cartridges having series of recesses wherein the single different concentrations of an experimental run have been determined one after another. The cartridges had to be cleaned in order to be reusable and in doing so, in view of the very sensitive method, the cleaning process could falsify the measured values due to residual traces resulting. Moreover, in using said single cartridges, whereas concentration changes can no more be exchanged by such having concentrations more conducive, the expenditure of time in comparison with the viability of the bioindicator only allowed the measurement of a restricted amount of different concentrations and, as the stretch of time increased, the reproducibility of the diverse measurements has not been granted, especially towards the end of the screening test.

Therefore, it is a subject of the invention to provide a method and a device wherewith a screening test for concentration-dependent reactions comprising a relatively great number of charges to be determined can be performed quickly and easily with such reactions where, in the course of a reaction to be tested, a reactant or indicator steadily loses activity and hence, the reaction is temporarily limited and can only be measured over a relatively short stretch of time. In particular, it should be made possible to measure the reactions using biological material especially bioindicators in the form of isolated cells or cell particles which show only a very restricted life-span in the reaction medium, the test results revealing a rate of reproducibility as great as possible. In this connection, it should be possible to determine those parameters that are correlated to the general effects of the substances on the bioindicator, in particular on electrophysiological parameters, that are depending from the concentration of one or several chemical substances, the concentration gradient of a test series being optimally adjustable on the vitality of each bioindicator being just used.

In determining concentration dependent parameters, especially in compiling dose-effect-relations, e.g. in using bioindicators in the "concentration-clamp method", the experimentalist is first confronted with the problem how sensitive will react each cell species used as bioindicator or the membrane patch being prepared from the cell species to the respective substance to be determined. The sensitivity not only depends from the actual vitality of the utilized bioindicator but also from the affinity of the chemical substance towards the receptors correlated with the ion channels of the bioindicator on the membrane surface of the cell species used, the effect of the substance on the bioindicator being usually unknown.

The present invention enables a person skilled in the art to discover the optimal concentration range together with the optimal gradient very quickly. The solutions containing the various concentrations are put into chambers (dishes) which are mounted on a round tray in a radial symmetric arrangement having equal distances one from another. Preferably, the fixation is performed by means of clips so as to grant an easy removal of the chambers fixed thereby and an exchange for chambers containing solutions of another concentration and/or substances. The round tray is stuck on a perpendicular motor shaft conveying the rotation of the computerized driving system control to the round tray. Said round tray can be easily removed from the shaft so as to grant a quick exchange for a round tray having another chamber arrangement with respect to the concentration or having chambers containing other biologically active substances.

Since the chambers located on the round tray can be exchanged repeatedly as well as there exists the feasibility to exchange for several round trays being arranged in varying manners, there can be measured optional concentration profiles of a run very quickly at a time. The single measurement of each concentration requires a very short stretch of time. In combining the suction and the measuring device to a measuring cell, the velocity of the single measuring process can be augmented once again. The measuring cell being immersed, the suction of each solution in a chamber into the suction tube requires only a few msec (depending from the viscosity of the solution between 2 and 100 msec), so that, at its active surface, the bioindicator is brought into contact with the solution to be measured very quickly.

The periodical horizontal rotation as well as the lifting or setting down of the round tray or of single chambers or the setting-down and lifting of the measuring cells are performed in each case via computerized control and hence are optimally synchronized.

In the same way, there is a computerized control as regards the succession of the measurements. In case that the chambers on the round tray are measured one after another according to the succession of their radial symmetric arrangement, prior to each measurement, the round tray rotates in each case by an angle of distance of two adjacent chambers. However, the present invention makes it possible, due to a program previously put in the computer or in accordance with the succession being provided by the computer from the previously measured actual values of the charges, that those chambers are measured one after another that are spaced, the tray rotating in each case in the direction of the shortest space of the spaced chambers.

In particular, it is thereby made possible to repeatedly measure the content of chambers being already measured previously and to compare the respective values with those measurements that have already taken place, due to a chronological or sequential space previously input into the computer. Thereby, the potential actual decay of the vitality of the used bioindicator can be noticed and, if necessary, taken into account by the computer when evaluating the measurements following up.

All in all, due to the computerized control of the movement of the round tray and/or of chambers and/or each used measuring cell in connection with the extremely quick measuring process in the measuring cell, even the stretch of time being required with the total testing of the series of measurements is so short, that the "life-span" of an isolated cell or an isolated membrane patch is sufficient to measure concentration series of different substances with one and the same bioindicator.

Hereby, optimal interpretations as to a comparative measurement of biological activities are made possible. The single concentrations of each substance to be measured are prepared over a great concentration range prior to the measurement; the chambers used are preferably made of throw-away material.

In the following, the object of the invention is closer exemplified by drawings.

Figure 1:
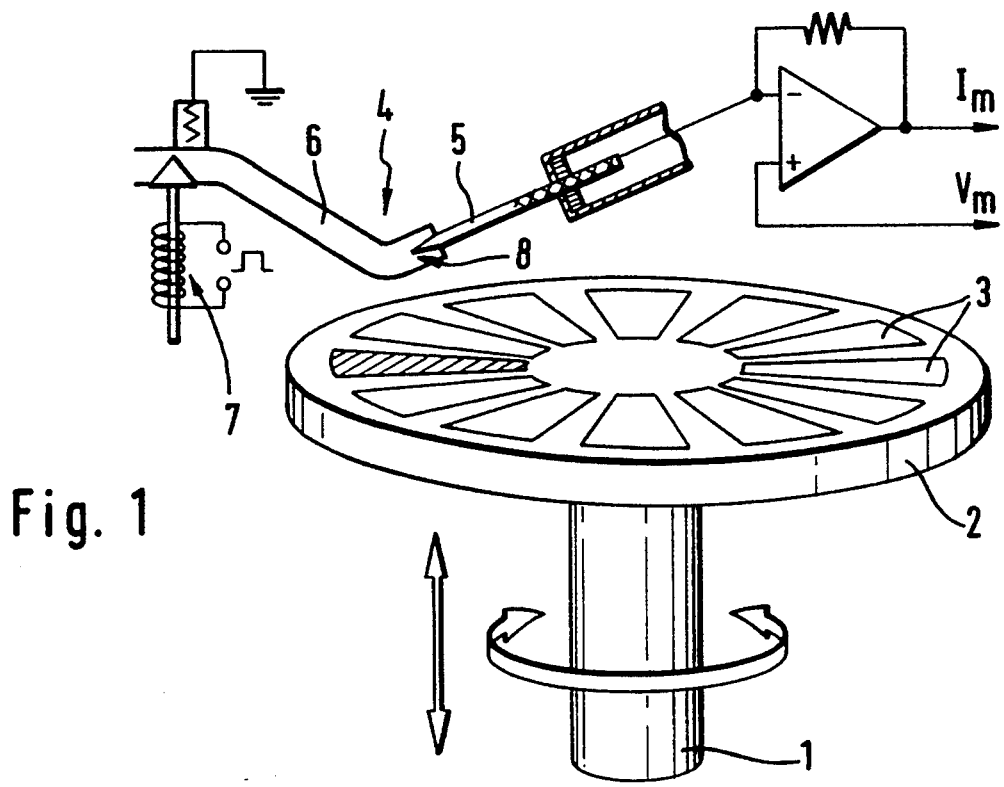
FIG. 1 shows the arrangement of a measuring cell and the round tray, the total round tray being additionally movable in vertical direction.

FIG. 1 shows a round tray 2 that can rotate round the vertical shaft 1 whereupon the single chambers 3 are arranged in radial symmetric manner. Preferably, the chambers are inserted into recesses adjusted to their form and are secured by clamps. The measuring cell 4 comprising a measuring pipette 5 and a suction tube 6 is positioned above the round tray. By means of a computerized process control, the chambers containing the desired concentration of biological active substance is moved underneath the measuring cell. As soon as the measuring cell is positioned above the chamber to be measured (hatching) the round tray is moved upwards by that amount until the measuring cell 4 immersess into the solution of the chamber. Instantly, the solution is drawn in via the suction tube being connected to a suction device in collaboration with the valve 7, and the electrophysiological parameter which is due to be determined is measured by means of the measuring pipette 5 and the attached cell 8 or the membrane patch. The total measuring process takes only some minor msec. Thereafter, the valve 7 reopens and the solution is taken away from this suction tube. Concurrently, the round tray is again lowered and, according to the computer program, the next chamber is moved under the measuring cell by means of a gyratory movement of the tray.

Figure 2:
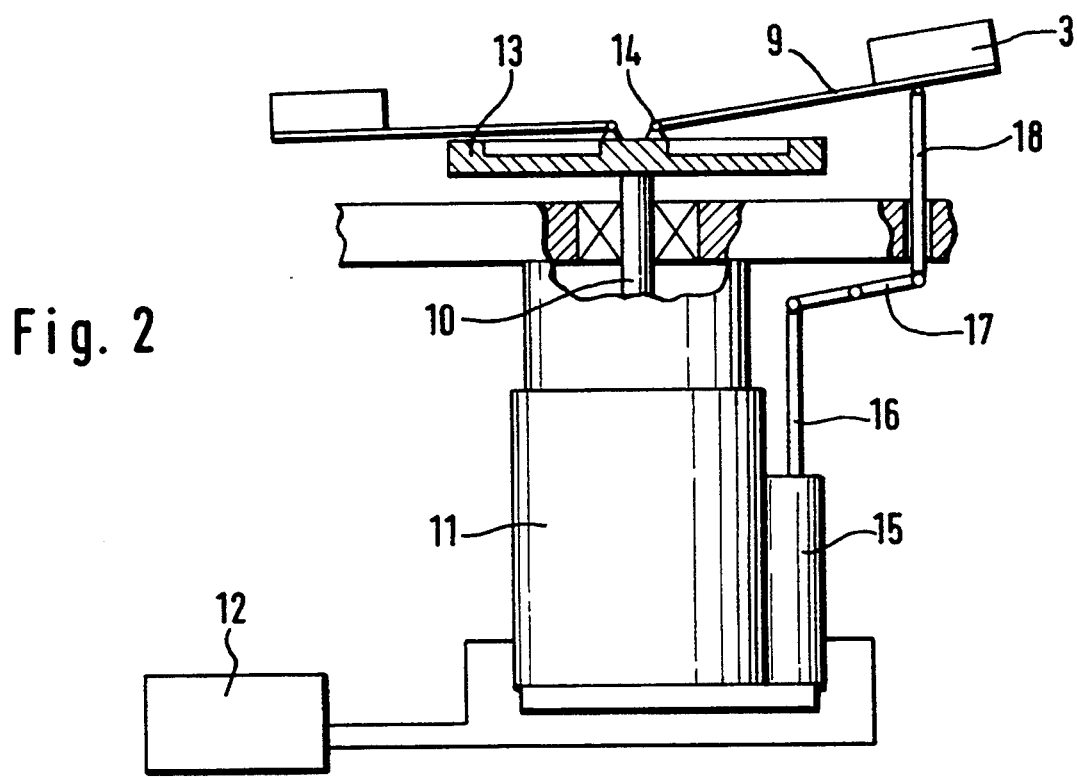
FIG. 2 shows a section through a round tray having a motor unit and a control unit, the chambers being individually movable in vertical direction.

FIG. 2 represents the section of a device, where the chamber 3 mounted on cantilevers 9 can be vertically lifted and then lowered as soon as said chambers are exactly positioned underneath the measuring cell by the gyratory movement of the round tray.

In said embodiment, the round tray comprises a rotary disk 13 whereupon cantilevers 9 together with the chambers 3 are mounted in radial symmetric fashion. The drive of the rotary disk 13 is performed by the vertical shaft 10 which, for its part, is moved by a motor, preferably by a piezomotor 11 that is controlled by a computerized control unit 12. The connection of the cantilevers 9 with the rotary disk 13 is performed by turning knuckles 14 having horizontal swiveling axis at the ends of the cantilevers 9 that are facing the pivot of the rotary disk. The cantilevers 9 can be swiveled round said turning knuckles in a vertical moving direction.

In this embodiment, the lift of the cantilevers 9 is mediated by means of a driving unit comprising a lifting rod 16 being moved by a driving device 15 that is also controlled by a computer, said lifting rod 16 transferring the movement via the lever 17 to the pusher 18 which finally upstrokes the chamber 3 being mounted on the cantilever 9.

What is claimed is:

1. Apparatus for determining concentration-dependent parameters by measurements of concentration-dependent electrophysiological effects on a bioindicator of a series of solutions each containing a concentration of at least one biologically active chemical substance correlated to the parameters, the parameters being determined by dependence on concentration of the chemical substance, said apparatus comprising:

means for measuring at least one of the parameters, the means being immersible in the solutions and being mounted on a vertical shaft, the means having a bioindicator attached thereto and being associated with an analyzer;

a round tray arranged in a plane below the measuring means, the round tray being mounted on a vertical shaft and rotatable around the shaft in a horizontal position, the round tray accommodating a plurality of chambers for the series of solutions comprising a run of measurements, each chamber containing a different concentration of chemical substance and being arranged in radial symmetry at equal distances one from another, at each single measurement the chamber with a solution to be measured being positioned in vertical alignment with the measuring means via a gyratory movement of the round tray so that by changing distance in a vertical direction between the measuring means and the round tray the measuring means is immersed into the solution contained in the chamber, the round tray comprising a rotary disk upon which lies a corona of cantilevers arranged in a radial symmetric orientation with respect to a center of rotation, the cantilevers being individually connected to a rotary disk by a pivoting joint comprising a horizontal rotation axis and each end of the cantilevers opposite to the center of rotation being displaceable in the vertical direction, an individual chamber being removably mounted on the end of the cantilever opposite to the center of rotation;

means for horizontally rotating the round tray bidirectionally around the shaft;

means for changing the vertical distance between the measuring means and a chamber positioned on the round tray, said means comprising means for lifting positions beneath the measuring device to lift the cantilever and chamber mounted thereon upwards to the measuring device and lower it again after measurement; and means for controlling the gyratory movement of the round tray and the reversible synchronized changes of the vertical distance in predetermined manner.

2. Apparatus according to claim 1, wherein the cantilevers project beyond the radius of the rotary disk, the lifting means of each cantilever situated beneath the measuring means comprising a plunger which displaces a cantilever from below at a position of the cantilever projecting beyond the radius of the rotary disk.

* * * * *